(12) United States Patent
Shi

(10) Patent No.: US 9,949,715 B2
(45) Date of Patent: Apr. 24, 2018

(54) SYSTEMS AND METHODS FOR ULTRASOUND PROBE GUIDANCE

(71) Applicant: General Electric Company, Schenectady, NY (US)

(72) Inventor: Xiaolei Shi, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 487 days.

(21) Appl. No.: 14/179,258

(22) Filed: Feb. 12, 2014

(65) Prior Publication Data

US 2015/0223772 A1 Aug. 13, 2015

(51) Int. Cl.
*A61B 8/00* (2006.01)
*A61B 8/08* (2006.01)

(52) U.S. Cl.
CPC ............ *A61B 8/0825* (2013.01); *A61B 8/429* (2013.01); *A61B 8/4236* (2013.01); *A61B 8/4245* (2013.01); *A61B 8/4427* (2013.01); *A61B 8/546* (2013.01)

(58) Field of Classification Search
CPC ... A61B 5/0062; A61B 5/0066; A61B 5/0084; A61B 5/0035; A61B 8/12; A61B 8/4461; A61B 5/0095; A61B 5/0086
See application file for complete search history.

(56) References Cited

U.S. PATENT DOCUMENTS

| | | | |
|---|---|---|---|
| 6,338,716 B1 | 1/2002 | Hossack et al. | |
| 6,511,427 B1 | 1/2003 | Sliwa et al. | |
| 6,554,771 B1 * | 4/2003 | Buil | A61B 8/00 600/424 |
| 8,328,725 B2 | 12/2012 | Anthony et al. | |
| 2006/0058654 A1 | 3/2006 | Di et al. | |
| 2009/0216121 A1 | 8/2009 | Lacoste | |
| 2009/0264768 A1 * | 10/2009 | Courtney | A61B 5/0062 600/463 |
| 2009/0306509 A1 | 12/2009 | Pedersen et al. | |
| 2012/0016239 A1 * | 1/2012 | Barthe | A61B 8/0858 600/439 |
| 2012/0251991 A1 | 10/2012 | Savitsky et al. | |
| 2012/0316407 A1 | 12/2012 | Anthony et al. | |
| 2013/0289411 A1 * | 10/2013 | Barnard | A61B 8/42 600/459 |

OTHER PUBLICATIONS

Mercier et al., "A Review of Calibration Techniques for Freehand 3-D Ultrasound Systems", Ultrasound Med Biol., vol. 34, Issue 4, pp. 449-471, Apr. 2005.

* cited by examiner

*Primary Examiner* — Joel Lamprecht
(74) *Attorney, Agent, or Firm* — Pabitra K. Chakrabarti

(57) ABSTRACT

Systems and method for ultrasound probe guidance are provided. One system includes a probe guide with a body having at least one engagement portion for coupling an ultrasound probe to the body. The system also includes at least one sensor configured to communicate with an ultrasound imaging system, wherein the at least one sensor coupled to the body and configured to determine at least one of a spatial position, an orientation, a probe head movement speed, a temperature, a scan speed of the body relative to an object being scanned, or a contact pressure relative to the body and the object being scanned.

29 Claims, 8 Drawing Sheets

SYSTEMS AND METHODS FOR ULTRASOUND PROBE GUIDANCE

BACKGROUND

Ultrasound imaging is an increasingly used tool for medical screening and early detection of breast cancer, especially for patients with dense breast tissue. Ultrasound systems may include either a handheld probe or an automated scanning system connected to an imaging system. These systems generate ultrasonic waves, which permeate the tissue of a patient, and partially reflect back to the source. A transducer then converts the reflected echo waves into electrical signals. The imaging system uses the electrical signals to construct images (e.g., two-dimensional or three-dimensional images.)

Handheld probes allow freeform movement, which makes it easier for an operator to scan, for example, various contours of a patient with the probe. However, because handheld probes have limited image reproduction capabilities, handheld probes have been generally used for diagnosis, not for screening.

Handheld probes also may rely on the skill of the operator, thereby limiting screening capabilities. For example, an unskilled practitioner may apply too much pressure on the tissue with the probe, causing the tissue to deform resulting in a distorted image. Conversely, not applying enough pressure may result in sub-optimal image quality. As another example, holding the probe at an oblique angle in relation to the tissue may also degrade image quality.

Handheld probes do not conventionally collect operational information that would allow an imaging system to assist the operator. Additionally, due to the free form nature of handheld systems, variations in image quality and inconsistent screenings may result from handheld imaging systems.

Automated whole-breast ultrasound systems are known that provide screening capabilities. However, automated systems may be bulky and/or costly. For example, some automated systems have a specially designed curved ultrasound probe with special immobilizer material between the tissue and the scan probe, which may be bulky. Other automated systems provide limited scan area coverage. Other systems provide no real-time feedback. Additionally, automated systems conventionally are not portable or easily portable. As such, automated systems are not a viable option for medical practitioners in developing countries.

SUMMARY

In accordance with an embodiment, a probe guide is provided that includes a body having at least one engagement portion for coupling an ultrasound probe to the body. The probe guide also includes at least one sensor configured to communicate with an ultrasound imaging system, wherein the at least one sensor is coupled to the body and configured to determine at least one of, a spatial position, an orientation, a probe head movement speed, a temperature, or a contact pressure the probe exerts on an object being scanned.

In accordance with another embodiment, an ultrasonic probe guide is provided that includes a body having at least one opening sized or shaped to receive a head of a transducer probe therein, wherein the body further includes an engagement portion configured to couple the transducer probe to the body with the head of the transducer extending into the opening. The ultrasonic probe guide also includes at least one sensor coupled to the body, wherein the at least one sensor is configured to communicate a spatial position, an angular orientation, a sweep speed across an object, or a contact pressure between the body and the object to an ultrasound imaging system. The ultrasonic probe guide further includes at least one status indicator coupled to the body, wherein the at least one status indicator is configured to communicate with at least one of the sensor or the ultrasound imaging system.

DETAILED DESCRIPTION

Figure 1:
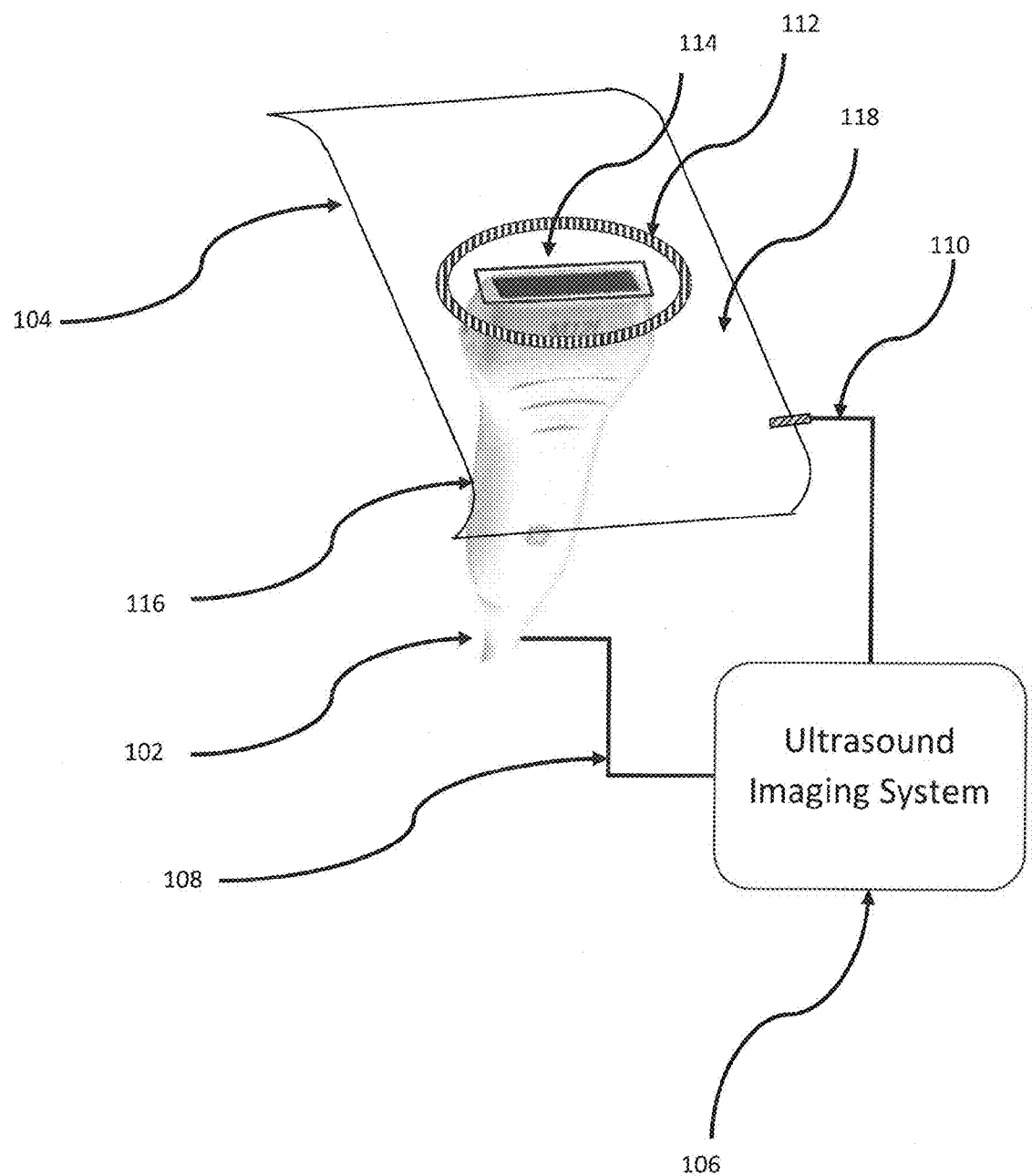
FIG. 1 is an illustration of a handheld ultrasound probe coupled to a probe guide body in accordance with an embodiment.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

In accordance with various embodiments, a probe guide is provided, which may be used in conjunction with an ultrasound imaging system. The imaging system may include an ultrasound probe that allows for, for example, two-dimensional (2D), three-dimensional (3D), or four-dimensional (4D) imaging. The probe guide in various embodiments is operable to be coupled to the head of a handheld probe (e.g., allowing the handheld probe to be retrofitted). The imaging system utilizes data from components of the probe guide and the probe to acquire information about the object being scanned (e.g., tissue of the patient). In addition, the probe guide may communicate with the ultrasound imaging system in order to provide guidance to an operator when scanning.

FIG. 1 is a perspective view of a handheld ultrasound probe 102 coupled to a probe guide having a probe guide body 104 in accordance with an embodiment. The ultrasound probe 102 is configured to interface with an ultrasound imaging system 106 through a communication link 108. Components of the guide body 104 interface with the ultrasound imaging system 106 through a communication link 110. The communication links 108 and 110 will be discussed in further detail below.

The probe guide body 104 in one embodiment is configured to be removably coupled to the ultrasound probe 102. For example, in the illustrated embodiment, the probe guide body 104 receives a probe head 114 (e.g., scanner head or portion) such that the ultrasound probe 102 may be coupled or decoupled to the guide body 104. As used herein, removably coupled generally refers to securing the guide 104 to the probe 102 such that the guide 104 and the probe 102 move together, thereby reducing or eliminating independent movement between the guide body 104 and the probe 102. Furthermore, the guide body 104 may be decoupled from the probe 102 (e.g., without damaging the probe 102). Thus, in various embodiments the probe guide body 104 is configured for removable coupling to the ultrasound probe 102.

However, it should be appreciated that the configurations are contemplated. For example, in various embodiments the probe guide body 104 may be fixedly secured or form part of the ultrasound probe 102 (e.g., forming an extended surface/structure for an ultrasound probe head to provide a guide for scan and to provide a platform to accommodate sensors and to achieve extended functions). Thus, in some embodiments, the probe guide body 104 is not removably coupled to the ultrasound probe 102, and may be permanently affixed thereto or form part of the probe (e.g., integrated or forms a unitary construction with the ultrasound probe 102). In some embodiments, the probe head of the ultrasound probe 102 may be packaged with the probe guide body 104.

The probe guide body 104 may include an engagement portion 112, which may be sized and shaped to receive a head of the probe 102 (identified as the probe head 114). When coupled together, in one embodiment, the engagement portion 112 provides a friction fit with the probe head 114. However, other coupling arrangements may be used as desired or needed.

The engagement portion 112 may be dimensioned (e.g., sized and shaped) to couple the guide body 104 to the probe head 114 in a fixed position or orientation relative to the guide body 104. The engagement portion 112 in some embodiments may be adjustable to receive probes heads of different sizes or shapes. Optionally, securing mechanisms (e.g., adhesives, putty, etc.) may be introduced between the probe head 114 and engagement portion 112. In some embodiments, additional securing means (e.g., screws, anchors, etc.) may be used to secure the probe 102 to the guide body 104.

In various embodiments, the body 104 may include a flange along the perimeter of the at least one engagement portion 112. The flange aligns and secures the engagement portion 112 to the probe head 114. The flange may be included to increase the contact area between the engagement portion 112 and the probe 102. The flange may encircle the perimeter of the engagement portion 112. Alternatively, the flange may only be present on one side of the engagement portion 112. In other embodiments, the flange may be present on two opposite sides of the engagement portion 112. It should be noted that the flange may be of varying size or shape as desired or needed. For example, the flange may be a rim, ridge, or lip, among other structures, surrounding the engagement portion 112.

Figure 2:
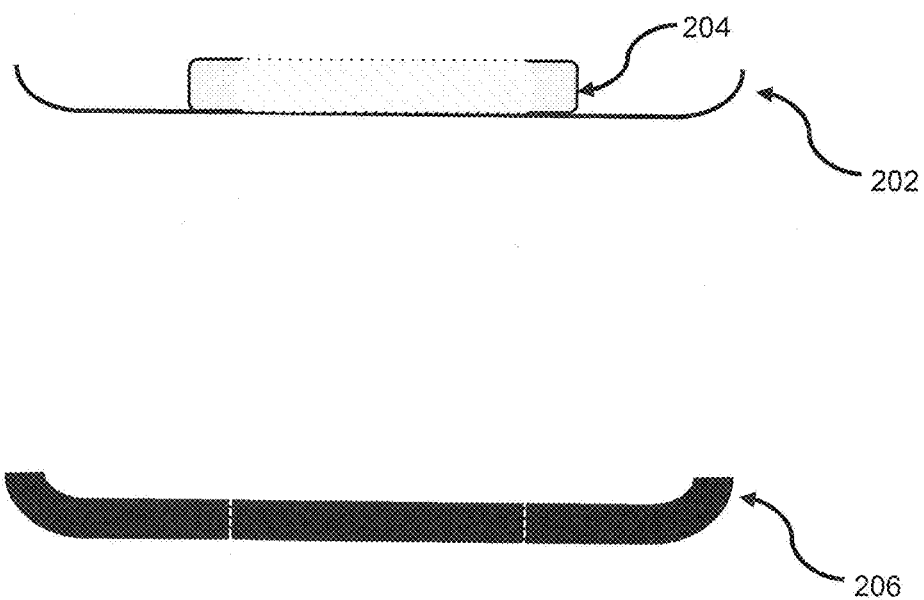
FIG. 2 illustrates cross-sectional side views of guide bodies in accordance with various embodiments.

FIG. 2 illustrates a cross sectional side view of different guide bodies in accordance with various embodiments. The guide body 202 includes a flange 204, and the guide body 206 does not the flange 206. The guide body 202 includes a flange 204 surrounding the perimeter of the engagement portion 208. In the configuration with the guide body 206, the guide body 206 may have a thickness dimensioned (e.g., sized and shaped) to receive and maintain therein the head of the ultrasound probe 114 without the use of the flange 204. For example, the guide body 206 may include sufficient internal structural material (e.g., thickness) to support the probe 102. The guide body 206 may have a uniform thickness as shown in FIG. 2. Optionally, the thickness of the guide body 206 may vary based on the size of the guide body 206 or may be thicker around the engagement portion (such as the engagement portion 112 shown in FIG. 1).

Figure 3:
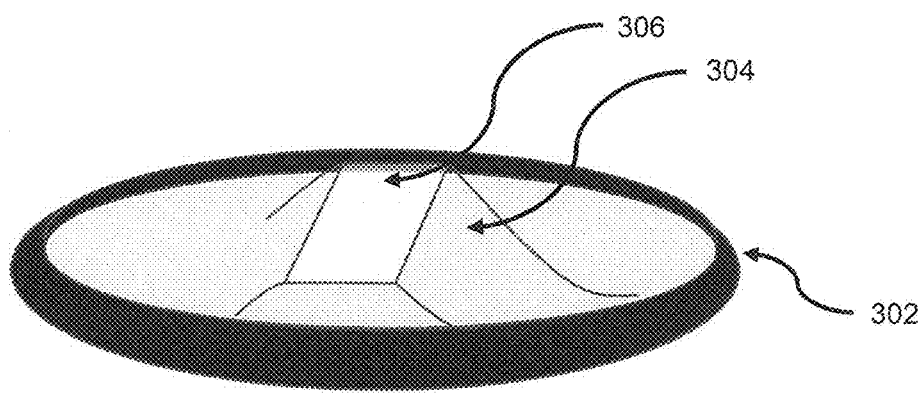
FIG. 3 illustrates a perspective view of a guide body configured with a raised flange in accordance with an embodiment.

FIG. 3 illustrates a perspective view of a guide body 302 configured with a raised flange 304 in accordance with an embodiment. In this embodiment, the raised flange 304 defines a substantial portion of the guide body 302. The guide body 302 includes the raised flange 304 along two opposite sides of the engagement portion 306.

In another embodiment, multiple probes 102 may be coupled to a single guide body 104. For example, the guide body in one or more embodiments may be configured with one or more engagement portions 114 to allow the guide body to couple to one or more probes 104. Each probe 104 may engage a different engagement portion 114.

In other embodiments, the engagement portion 114 may be configured with an adapter plate (not shown) to allow the engagement portion 114 to receive a probe having a dimension not compatible with the engagement portion 114.

Figure 4:
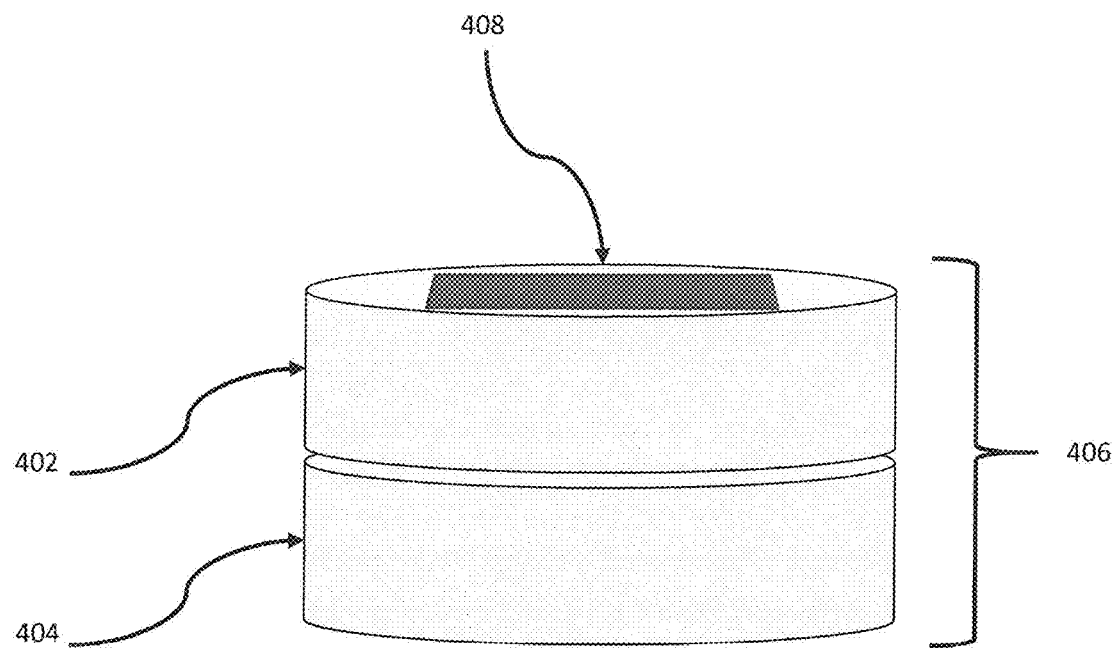
FIG. 4 illustrates a guide body assembly in accordance with an embodiment.

In another embodiment, one or more guide bodies 104 may be coupled to a probe 102 to form a guide body assembly. For example, FIG. 4 illustrates an embodiment of a guide body assembly. A guide body assembly in the illustrated embodiment includes two or more guide bodies 104 coupled to one another (illustrated in a stacked arrangement). As shown in FIG. 4, the guide bodies 402 and 404 are joined (which may be fixed or removably coupled) to form the guide body assembly 406. The guide body 402 and guide body 404 may be the same or have different configurations, as well as be the same or different than the guide body 104. The guide body 402 may be coupled to guide body 404 with a friction fit. For example, the engagement portion 408 of guide body 402 may be configured to align and friction fit with the engagement portion (not shown) of the guide body 404. However, other coupling arrangements may be used as desired or needed.

The guide bodies 402 and 404 may be selectively arranged in the assembly 406 to combine or enhance the capabilities sensing capabilities. As an example, the guide body 404 may be configured with a pressure sensor, thus the guide body 404 may be placed below guide body 402 to allow the pressure sensor to contact with the tissue of the patient. As another example, the guide body 402 may include a line-of-sight type location marker. In this example, the guide body 402 may occupy the upper portion of the assembly 406. Once coupled to the guide body assembly 406, the head of the probe 102 may extend through the assembly 406. It should be noted that in the various embodiments, the head of the probe may extend partially or completely through a respective engagement portion.

Figure 5:
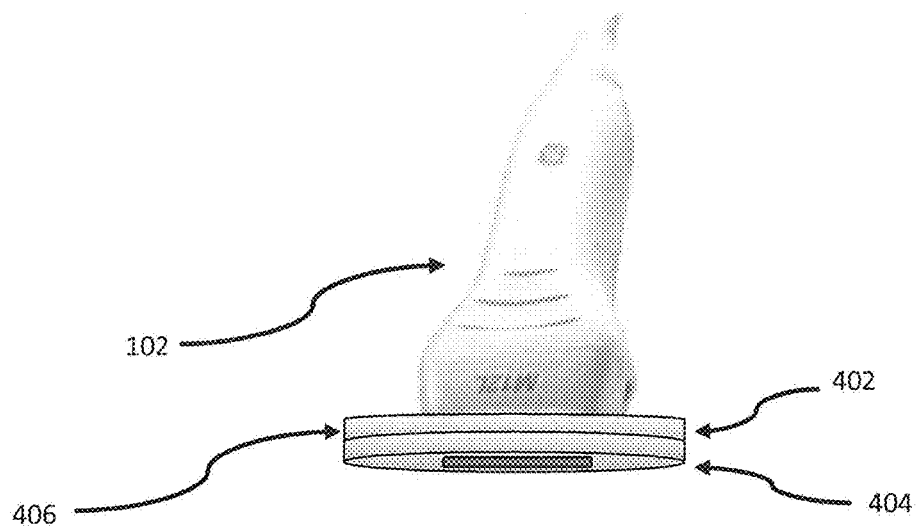
FIG. 5 illustrates the guide body assembly coupled to a probe head in accordance with an embodiment.

FIG. 5 illustrates the assembly 406 of FIG. 4 coupled to the probe head 102 in accordance with an embodiment. In this embodiment, the guide bodies 402 and 404 form the assembly 406, which couples to the probe head 102 and maintains the position and orientation of the probe with respect to the assembly 406. In another embodiment, the guide body 402 and 404 may couple to the probe head 102 and not to one another.

Figure 6:
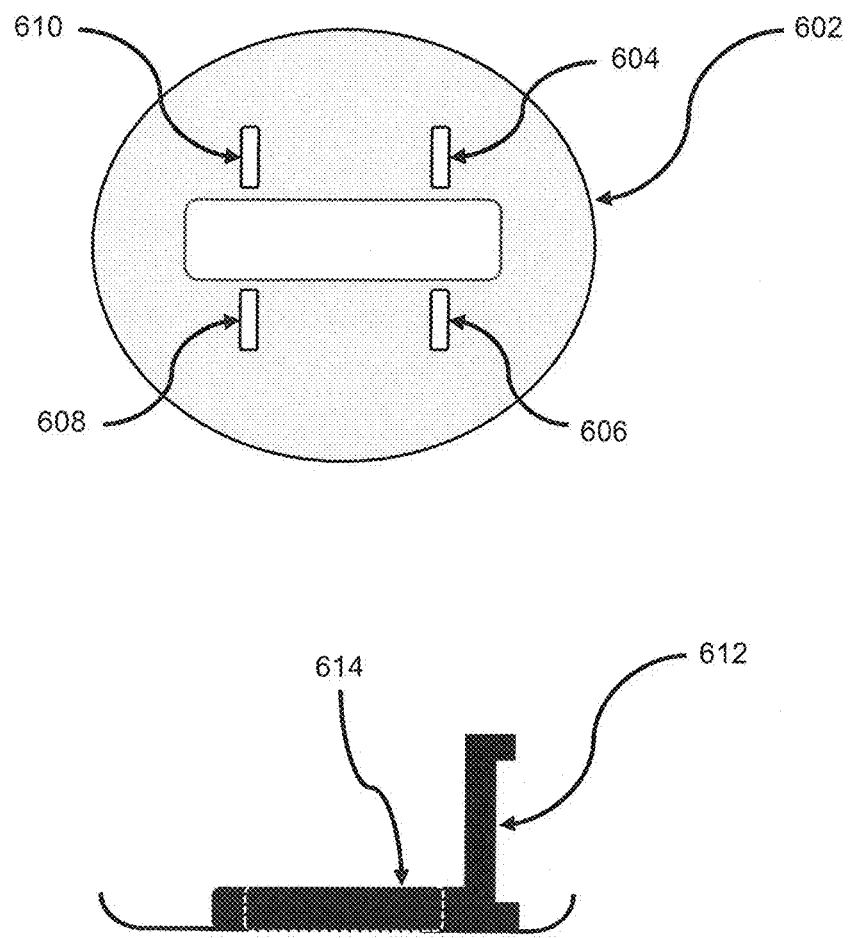
FIG. 6 illustrates a guide body having a sensor or location marker removably secured thereto in accordance with an embodiment.

Turning now to the embodiment illustrated in FIG. 6, the guide body 104 may further be configured to removably couple at least one device, such as a sensor to the guide body 104. FIG. 6 illustrates top and side views of a guide body 602 configured to removably couple a sensor thereto body in accordance with an embodiment. In one embodiment, the guide body 602 may include an aperture to receive a sensor. For example, the guide body 602 may include openings 604, 606, 608 and 610 (or other types of mounting portions) to receive sensors within the openings. The openings 604-610 may be selectively dimensioned (e.g., sized and shaped) based on the type of sensor to be received in and/or coupled thereto.

In some embodiments, the guide body 104 may include a clamping structure 614 to receive and support a sensor on the top of the body 104. For example, the guide body 612 may include the clamping structure 614 to receive and secure a sensor. The clamping structure 614 may be a structure extending radially away from the guide body 612. Optionally, the clamping structure 614 may create a bracket in which the sensor may be received and provide a friction fit. The clamping structure 614 may be selectively located on the guide body 612 based on the type of sensor. For example, a position sensor may require line-of-sight communication with the imaging system 106, in which case, the clamping structure 614 may position the sensor away from the probe 102.

The various embodiments of guide bodies or engagement portions 112 may be formed of a material (e.g., plastic) to allow the body 104 or the engagement portion 112 to be sufficiently resilient in order to be repeatedly coupled and decoupled to the probe 102 (e.g., without loss of elasticity). In other embodiments, a rigid material may be used that resists deformation under normal load while remaining lightweight. Optionally, the guide body 104 may be made of the same or different material as any of the other components. For example, the engagement portion 112 may be made from an elastomer, whereas the guide body 104 may be made from plastic.

The guide body 104 in some embodiments may be shaped for smooth movement or translation over the surface of the patient. In one embodiment, the guide body 104 may include a curved edge 116 along at least two opposite sides. As another one embodiment, the curved edge 116 extends along or around the perimeter of the guide body 104. The radius of curvature of the curved edge 116 may be based, for example, on the dimensions of the body 104, the particular application, the type of probe, etc. For example, a body 104 having a thickness of 3 centimeters may have a radius of curvature of 2 centimeters (e.g. rounded). However, different dimensions may be used as desired or needed. As another example, a body 104 having a thickness of 1 centimeter may have a radius of curvature of 0.5 centimeter (e.g., generally blunt edge).

The guide body 104 may be provided in different shapes. In one embodiment, the guide body 104 is in a planar form and symmetric. For example, the guide body 104 may be circular, elliptical, or quadrilateral. In one embodiment, the guide body 104 may be circular measuring 5 centimeters in length from an outside edge of the probe 102 and 1 centimeter thick. However, different dimensions may be used as desired or needed. For example, for a breast scan application, the guide body dimensions may be sized (e.g., <10 cm) to ensure contact with curved breast surface. In various embodiments, the guide body 104 is sized and shaped to ensure good mechanical stability and ergonomic operation. For example, in some embodiments, the guide body 104 has a length and/or width that is less than about 10 centimeters from an outside edge of the probe.

The guide body 104 in various embodiments includes a laminar surface 118 substantially perpendicular to the probe head 114. The perpendicular relationship between the surface 118 and the probe 104 encourages and/or maintains the probe head 114 perpendicular to the surface of the subject. Because the laminar surface 118 of the guide body 104 is perpendicular to the probe head 114, and generally parallel to the surface of the breast tissue, the guide body 104 keeps the probe head 114 perpendicular to the surface of the breast tissue. By practicing various embodiments, which may include maintaining the probe 102 in a perpendicular orientation in relation to the subject, enhanced image quality may be provided. For example, in one embodiment the guide body 104 may be used in conjunction with an ultrasound imaging system to support ultrasonic examination of breast tissue. Maintaining the probe 102 in a perpendicular orientation with respect to the breast tissue may reduce scan artifacts from reflections and refraction, and may further increase the volume of coverage. Thus, the probe guide 104 facilitates an operator orienting the probe 102 to enhance the image quality.

Figure 7:
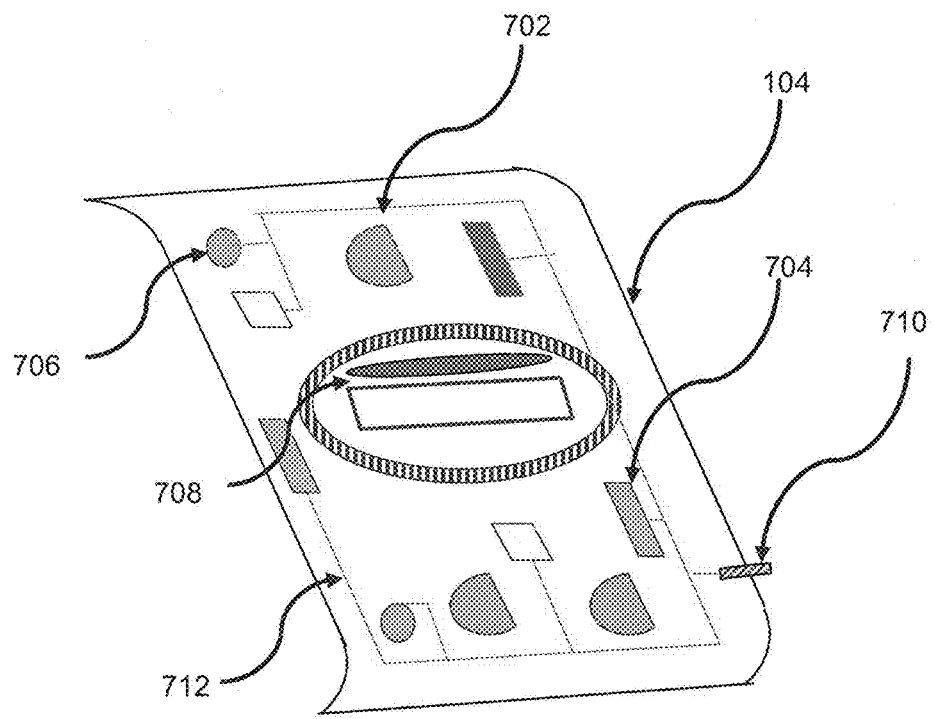
FIG. 7 is an illustration of the probe guide body of FIG. 1 in accordance with an embodiment.

Various embodiments of the probe guide may include different elements or components for facilitating alignment and use, for example, as shown in FIG. 7, with respect to the probe guide body 104. The guide body 104 may include at least one position marker 702 integrated within or coupled with the guide body 104. The position marker 702 provides a spatial reference point. The position marker 702 may be, for example, any optical or electromagnetically distinguishing feature as is known in the art. For example, the position marker 702 may be a dot or a series of dots (e.g. permanent dot marks). As another example, the position marker 702 may be a pattern of marks such as a grid or a dot array. As another example, the position marker 702 may be a bar code or quick response (QR) code. As another example, the position marker 702 may be a magnet. As another example, the position marker 702 may be infrared reflective material. As another example, the position marker 702 may be a radio frequency identification (RFID) tag.

The position marker 702 allows the imaging system 106 to determine the position of the guide body 104 in relation to a predetermined reference point. The imaging system 106 determines the position of the guide body 104, for example, by measuring the displacement of the position marker 702 in three dimensions relative to the predetermined reference point. For example, the predetermined reference point may be the intersection of a first and a second edge of an imaging platform. In this example, the imaging system 106 may use the position marker to calculate the longitudinal position of the guide body 104 in relation to the first edge and the lateral position of the guide body 104 in relation to the second edge of the imaging platform. Accordingly, the imaging system 106 may use the position marker 702 to determine the height of the guide body 104 above the surface of the imaging platform. Thus, the position marker 702 allows an imaging system 106 to determine the location of the guide body 104 in three dimensions relative to the reference point. For example, U.S. Pat. No. 6,338,716 describes one method that may be used to determine the spatial orientation and location of ultrasound probes using reference points.

In another embodiment, the position marker 702 may communicate with another medical diagnostic system (e.g., remote from the ultrasound system or imaging system 106). For example, the position marker 702 may communicate with an IR tracking system. The position marker 702 may also communicate with one or more imaging systems concurrently. For example, the position marker 702 may communicate with the imaging system 106 and an IR tracking system concurrently. The imaging system 106 may then correlate data from the IR tracking system with the image data.

The position marker 702 may be selectively positioned on the guide body 104 so that the location of the position marker 702 may be representative of the location of the probe 102. For example, the position marker 702 may be located near the engagement portion 112. Optionally, the position marker 702 may be positioned to avoid obstruction by the guide body 104 or the probe 102. For example, the position marker 702 may be located on an outer edge to allow line-of-sight type optical systems to detect the position marker. It should be appreciated that the body 104 may contain more than one position marker and the position marker 702 may be of the same or different types.

In another embodiment, the guide body 104 may include at least one sensor 704 coupled thereto. The sensor 704 senses the physical or operational state of guide body 104. Because the guide body 104 and the probe 102 move together when coupled to one another, operating characteristics, conditions, or physical state information from the sensor 704 may be representative of the operation of the probe 102. The physical state sensed by the sensor 704 may include at least one of an angular orientation, a spatial position, a probe head 114 movement speed, a contact pressure, or a temperature.

The angular orientation may include the angular orientation of the guide body 104 about a single or multiple axes. For example, the Euler angles in relation to the plane of the guide body 104 may represent the angular orientation. The spatial position may be at least one of the lateral, the longitudinal, or the vertical position of the guide body 104. Any technology as is used in the art may sense the spatial and angular orientation. For example, the sensor 704 may be an accelerometer, a gyroscope, or MEMS, among other sensors.

The probe head movement speed represents the speed of movement of the probe head 114 in relation to the subject. The probe head movement speed may be sensed using infrared or a similar sensor as is known in the art. Optionally, the imaging system 106 may calculate the probe head movement speed by tracking the speed of the movement of the guide body 104 relative to an imaging platform.

The contact pressure represents the force applied by the guide body 104 onto the subject. The contact pressure may be at least one of a normal, a torsional, a rotational, a compressional, or a shear force applied by the pressure to the tissue. For example, the sensor 704 may be a strain gauge configured to measure the normal force applied by pressure to the surface of the tissue.

In another embodiment, the sensor 704 may be a temperature sensor. The temperature sensor may be configured to sense the temperature of the surface of the tissue. Alternatively or optionally, the temperature sensor may be configured to sense the temperature of the ambient environment. Alternatively or optionally, the temperature sensor may be configured to sense the temperature of the probe head 102.

It should be appreciated that the guide body 104 may be configured with more than one sensor or sensor type (such as multiple sensors of the same or different type). Furthermore, the sensors may be placed at select locations on the body 104 to provide a defined or needed sensor accuracy.

In another embodiment, the guide body 104 include at least one status indicator 706 (e.g., coupled thereto). The status indicator 706 may provide feedback with visual or aural cues to the operator. For example, the status indicator 706 may be a speaker. As another example, the status indicator 706 may be a light. As another example, the status indicator 706 may be a display. The status indicator 706 may interact with the one or more sensors 704 to provide feedback based on at least one of a select pressure level, a probe head 114 movement speed, a gel status, a wireless connection status, or a temperature, as described in more detail herein.

Alternatively or optionally, the status indicator 706 may provide feedback based on information received from the imaging system 106. For example, the imaging system 106 may wirelessly communicate with the status indicator through a communication module 710. The imaging system 106 may then instruct or control the status indicator 706 to provide, for example, an aural cue when the operator applies a pressure greater than 0.5 N. As another example, when the imaging system 106 determines the applied pressure exceeds a predetermined threshold, the imaging system 106 may instruct or control the status indicator 706 to illuminate a light emitting diode. As another example, the imaging system 106 may communicate with the status indicator 706 to provide directional guidance to recreate a previously performed scan (e.g., using stored scan coordinates and probe location information). Furthermore, the status indicator 706 may communicate with another medical diagnostic system. For example, the status indicator 706 may communicate with the imaging system 106 and an IR mapping system concurrently.

In another embodiment, the status indicator 706 may communicate with components onboard the body 104 in addition to the medical imaging system 106. For example, the status indicator 706 may be embodied as a liquid crystal display and may be configured to display the temperature provided by the sensor 704. When configured as a display, the indicator 706 may also show the status of the communication link 110. As another example, the status indicator 706 be embodied as an audible device or tactile device, and may be configured to provide a warning when the acoustic fluid quantity in the gel dispenser 708 reaches a predetermined level.

In one embodiment, the guide body 104 may include a gel dispenser 708 that may provide automatic gel dispensing. In various embodiments, automatic application of an acoustic fluid (e.g., ultrasound gel) streamlines operator workflow and enhances efficiency. The gel dispenser 708 introduces acoustic between the guide body 104 and the object being scanned (e.g., tissue). It should be noted that the gel dispenser 708 may be embodied as a recess or channel along the surface of the body 104 on the side that contacts the tissue (e.g., the bottom), thus allowing the distribution of acoustic fluid between the tissue and the guide body 104. For example, the channel may extend around the perimeter of the body 104 and terminate at an aperture. The aperture may extend to the top of the body 104 where acoustic fluid may be introduced. The acoustic fluid then travels through the body 104 to fill the channel.

In another embodiment, the gel dispenser 708 may be configured to automatically dispense acoustic fluid based upon sensor readings. For example, the gel dispenser 708 may be configured to automatically dispense acoustic fluid based on a predetermined scan speed. Alternatively or optionally, the gel dispenser 708 may be configured to automatically dispense a predetermined amount of acoustic fluid based on temperature. Alternatively or optionally, the imaging system 106 may determine when to apply to apply the acoustic fluid.

The communication module 710 in various embodiments exchanges information between the body 104 and the imaging system 106. The body 104 may be configured with communication lines, illustrated as wiring 712 connecting the communication module 710 with at least one of the sensor(s) 704, the status indicator 706, or the gel dispenser 708. In one embodiment, the communication module 710 exchanges information between the sensor 704 and the status indicator 706. The communication module 710 may exchange information between the sensor 704 and the imaging system 106. In some embodiments, the communication module 710 may exchange information between a status indicator 706 and the imaging system 106. For example, the communication module 710 may transmit position data sensed by the sensor 704 to the imaging system 106. As another example, the communication module 710 may transmit orientation, data sensed by the sensor 704 to the imaging system 106. As another example, the communication module 710 may transmit probe head 114 movement speed sensed by the sensor 704 to the imaging system 106. As another example, the communication module 710 may transmit the pressure applied by an operator sensed by the sensor 704 to the imaging system 106. As another example, the communication module 710 may transmit information received from the imaging system 106 to the status indicator 706. As another example, the communication module 710 may transmit instructions received from the imaging system 106 to the gel dispenser 708.

The communication module 710 may establish a communication link 110 with the imaging system 106. Optionally or alternatively, the communication module 710 may establish a communication link with another medical diagnostic system. Optionally or alternatively, the communication module 710 may establish a communication link 110 with multiple imaging systems 106 concurrently. For example, the sensor 704 configured as a pressure sensor may communicate with a medical imaging 106 system while another sensor 704 configured as a temperature sensor communicates with the gel dispenser 708. In another embodiment, the communication module 710 may be integrated with other test modalities. For example, the communication module 710 may interact with an electrical impedance tomography (EIT) imaging system. As another example, the communication module 710 may interact with a photo-acoustic tomography (PAT) imaging system. As another example, one or more features or components (e.g., an interface) may be provided for other test modalities, for example, to position an array of optical fibers for photo-acoustic imaging. The optical fibers may be physically coupled to the probe guide and operate with the ultrasound probe to obtain photo-acoustic imaging for the object under scan.

The communication module 710 may be configured with transceivers as is known in the art. The communication link 110 may be a wired or a wireless link. For example, the wireless connection may be one of, RF, WiFi, Zigbee, Bluetooth, IR, and the like. In another embodiment, the communication link 110 may be a wired connection to the imaging system 106. The wired connection 110 may employ a separate wire than used to connect the handheld probe 102 to the imaging system 108.

Figure 8:
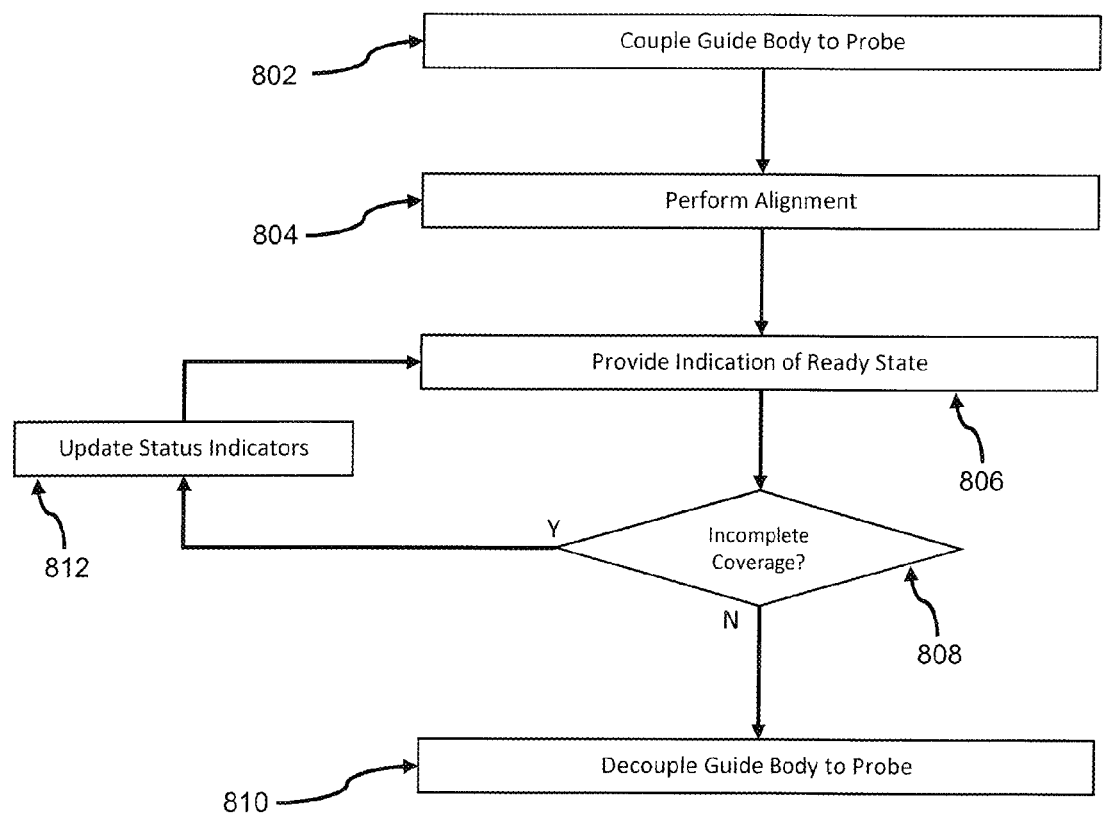
FIG. 8 is a flowchart of a method in accordance with an embodiment.

FIG. 8 is a flowchart illustrating a method 800 in accordance with various embodiments. The method 800, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the methods may be able to be used as one or more algorithms to direct hardware to perform operations described herein.

The method 800 includes at 802, coupling the guide body 104 to probe head 114. The probe head 114 is aligned and is secured into the engagement portion 112 of the guide body 104. Once coupled, the probe head 114 extends through the guide body 104 in some embodiments. Optionally, additional securing means may be used to couple the guide body 104 to the ultrasound probe 102 as described herein.

At 804, the imaging system performs an alignment to calibrate the location of the guide body 104 in relation to the ambient environment. The calibration process spatially correlates position and angular orientation data from the position marker 702 and the one or more sensors 704 with predetermined correlation values. The calibration technique may be any orientation resolution technique as is known in the art. For example, the imaging system 106 may instruct the operator (e.g., provide a notification on the status indicator 706) to trace a predetermined path.

At 806, the imaging system 106 instructs the status indicator 706 to indicate a ready state. The ready state indication informs the operator that the system is ready to perform a scan. For example, the status indicator 706 may be configured with an audible device, which sounds when the imaging system 106 indicates a ready state. As another example, the status indicator 706 may be configured as a display, which provides a visual notification when the imaging system 106 indicates a ready state.

While a scan is in progress, the imaging system 106 collects data from the one or more sensors 704. For example, the imaging system may continuously monitor at least one of the position, orientation, or pressure readings from the sensor(s) 704 while capturing image data and providing feedback to the operator with lights or sounds through the status indicator 706. The imaging system 106 may temporally and spatially correlate data from the sensor 704 with an ultrasound image generated from image data acquired by the ultrasound probe 102. Correlating data from sensors allows the imaging system 106 to determine whether coverage is complete for a given test area. If for example, when data from the sensor 704 exceeds predetermined threshold levels, the imaging system 106 determines that scan coverage is incomplete at that location. For example, if the sensor 304 indicates the applied pressure exceeds 0.5 N while scanning a select region of tissue, then the imaging system 106 determines coverage to be incomplete at that region. Optionally, when the imaging system 106 indicates coverage to be incomplete, the imaging system 106 may instruct the status indicator 706 to provide feedback to the operator. For example, the status indicator 706 may provide an aural cue when the applied pressure exceeds 0.5 N.

At 808, the imaging system determines whether coverage is complete. If coverage is incomplete, then at 812, the imaging system instructs the status indicator 706 to provide indication of incomplete coverage. The operator may then decide to rescan the select region of incomplete coverage. At 808, if a determination is made that scan coverage is complete, at 810, the probe guide body 104 is decoupled from the probe 102.

In various embodiments, the sensor data (position/orientation) may be used with ultrasound image data to form 3D (more accurate) images of the object under scan, which may help with disease identification and be used for problem tracking in future disease treatment workflow. In various embodiments, the sensor data may be used for scan quality control. For example, the data may be reported together with the image data to validate the scan operation, which can be beneficial to patients. In some embodiments, the sensor data may be used to qualify whether the scan operation, and accordingly the ultrasound images, are acceptable (e.g., provide acceptable diagnostic information or meet an acceptable image level).

Thus, various embodiments provide a probe guide to facilitate scanning or screening using an ultrasound probe.

It should be noted that different processing elements or memory devices or storage may be provided in connection with the various embodiments.

It also should be noted that the various embodiments may be implemented in hardware, software or a combination thereof. The various embodiments and/or components, for example, the circuits, or components and controllers therein, also may be implemented as part of one or more computers or processors. The computer or processor may include a computing device, an input device, a display unit, and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "circuit" may include any processor-based or microprocessor-based system including systems using microcontrollers, reduced instruction set computers (RISC), SISCs (e.g., ARM processors), ASICs, logic circuits, and any other circuit or processor capable of executing the functions described herein. The above examples are exemplary only, and are thus not intended to limit in any way the definition and/or meaning of the term "computer."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or circuits, a program circuit within a larger program or a portion of a program circuit. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, paragraph f, unless and until such claim limitations expressly use the phrase "means for" followed by a statement of function void of further structure.

This written description uses examples to disclose the various embodiments to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. An ultrasound probe guide comprising:
    a body having at least one engagement portion configured to receive a probe head of an ultrasound probe to couple the ultrasound probe to the body, wherein the body is planar having curved edges along opposite sides of the body,
at least one sensor attached to or within a surface of the body wherein the sensor is configured to communicate with an ultrasound imaging system through a communication link,
the at least one sensor configured to determine at least one of a spatial position, an orientation, the probe head movement speed, a temperature, or a contact pressure the ultrasound probe exerts on an object being scanned.

2. The ultrasound probe guide of claim 1, wherein the body includes at least one status indicator configured to communicate with at least one of the sensors or the imaging system.

3. The ultrasound probe guide of claim 2, wherein the at least one status indicator further comprises of at least one of an aural or visual device.

4. The ultrasound probe guide of claim 1, wherein the at least one sensor is further configured to wirelessly communicate with the ultrasound imaging system.

5. The ultrasound probe guide of claim 1, wherein the body includes at least one status indicator configured to wirelessly communicate with the at least one sensor or the ultrasound imaging system.

6. The ultrasound probe guide of claim 1, wherein the body includes at least one position marker arranged to provide a spatial reference point to the ultrasound imaging system.

7. The ultrasound probe body of claim 1, wherein the body includes a gel dispenser, the gel dispenser having at least one of an opening or a channel to dispense an acoustic fluid between the probe head of the ultrasound probe and the object.

8. The ultrasound probe guide of claim 1, wherein the body has a length less than 10 centimeters from an outside edge of the probe.

9. The ultrasound probe guide of claim 1, wherein the ultrasound imaging system is configured to temporally and spatially correlate data from the at least one sensor with an image generated by the ultrasound imaging system.

10. The ultrasound probe guide of claim 1, wherein the at least one sensor is configured to communicate with another medical diagnostic system through a second communication link.

11. The ultrasound probe guide of claim 1, wherein the body includes at least one opening configured to receive the at least one sensor.

12. The ultrasound probe guide of claim 1, wherein the body comprises at least one interface of a communication module configured to position an array of optical fibers for photo-acoustic imaging.

13. The ultrasound probe guide of claim 1, wherein the body includes at least one flange along a perimeter of the at least one engagement portion, wherein the flange is configured to align the engagement portion to the probe head.

14. The ultrasound probe guide of claim 13 wherein the flange defines the thickness of the probe body.

15. The ultrasound probe guide of claim 1, wherein the body is configured to receive a second probe head of a second ultrasound probe, the probe head having a different size or shape relative to the second probe head.

16. The ultrasound probe guide of claim 1, wherein the body includes a laminar surface configured to maintain a perpendicular orientation between the probe head and the object.

17. The ultrasound probe guide of claim 1, wherein a size and shape of the engagement portion is configured to provide a friction fit with the probe head received by the engagement portion.

18. An ultrasonic probe guide comprising:
a body having at least one opening sized or shaped to receive a probe head of a transducer probe therein, the body further including an engagement portion configured to couple the transducer probe to the body with the probe head of the transducer extending into the opening, wherein the body is planar having curved edges along at least two opposite sides, wherein the body includes at least one sensor attached to or within a surface of the body wherein the sensor is configured to communicate at least one of a spatial position, an angular orientation, a sweep speed across an object, or a contact pressure between the body and an object being scanned, to an ultrasound imaging system through a communication link.

19. The ultrasonic probe guide of claim 18, wherein the body includes at least one status indicator configured to communicate with the at least one sensor or the ultrasound imaging system.

20. The ultrasonic probe guide of claim 19, wherein the at least one status indicator communicates wirelessly with the ultrasound imaging system.

21. The ultrasonic probe guide of claim 18, wherein the at least one sensor is configured to communicate wirelessly with the ultrasound imaging system.

22. The ultrasound probe guide of claim 18, wherein the body includes a laminar surface configured to maintain a perpendicular orientation between the probe head and the object.

23. The ultrasound probe guide of claim 18, wherein a size and shape of the engagement portion is configured to provide a friction fit with the probe head received by the opening.

24. A method comprising:
configuring an ultrasonic probe guide to be coupled with a handheld ultrasound probe, the ultrasonic probe guide having a body that includes an engagement portion configured to receive a probe head of the handheld ultrasound probe, and the ultrasound probe is configured to maintain a fixed position of the handheld ultrasound probe coupled thereto with the body, wherein the body is planar having curved edges along at least two opposite sides;
at least one of a sensor, a position marker or a status indicator attached to or within a surface of the body, wherein the sensor, the position marker or the status indicator is configured to communicate with an ultrasound imaging system through a communication link; and
configuring the sensor, the position marker or the status indicator to provide status or guidance information at the probe.

25. The method of claim 24, wherein configuring the sensor, the position marker or the status indicator to provide status or guidance information comprises configuring the sensor, the position marker or the status indicator to provide feedback with aural or visual notifications.

26. The method of claim 24, further comprising providing the body of the ultrasonic probe guide as a planar member having curved edges along at least two opposite sides.

27. The method of claim 24, further comprising acquiring ultrasound imaging data with the probe and using data from the at least one sensor with the ultrasound imaging data to form a three-dimensional image of an object being scanned by the probe.

28. The method of claim 24, wherein a size and shape of the engagement portion is configured to provide a friction fit with the probe head received by the engagement portion.

29. The method of claim 24, wherein configuring the ultrasonic probe guide for coupling with a handheld ultrasound probe comprises configuring the engagement portion to receive a second probe head of a second probe head of a second handheld ultrasound probe, the probe head having a different size or shape relative to the second probe head.

* * * * *